United States Patent
Jow et al.

(10) Patent No.: US 7,988,844 B2
(45) Date of Patent: Aug. 2, 2011

(54) METHOD FOR MEASURING AN IODINE ADSORPTION NUMBER OF CARBON BLACK, ELECTROLYTIC CELL, AND KIT FOR MEASURING AN IODINE ADSORPTION NUMBER OF CARBON BLACK

(75) Inventors: Jiin-Jiang Jow, Kaohsiung (TW);
Ho-Ruei Chen, Kaohsiung (TW);
Ping-Feng Lo, Kaohsiung (TW);
Zong-Sin Guo, Chiayi County (TW);
Tzong-Rong Ling, Kaohsiung County (TW)

(73) Assignee: National Kaohsiung University of Applied Sciences, Kaohsiung (TW)

( * ) Notice: Subject to any disclaimer, the term of this patent is extended or adjusted under 35 U.S.C. 154(b) by 203 days.

(21) Appl. No.: 12/462,705

(22) Filed: Aug. 7, 2009

(65) Prior Publication Data

US 2011/0031128 A1 Feb. 10, 2011

(51) Int. Cl.
*C25B 15/02* (2006.01)
*G01N 27/26* (2006.01)

(52) U.S. Cl. ............... 205/335; 205/778.5; 205/779.5; 204/400; 204/412; 204/228.6; 204/228.9; 204/229.1; 204/229.9; 204/230.1; 204/230.7; 204/242; 422/807; 422/808; 422/430; 422/62; 422/68.1; 422/69; 422/72; 422/82.1; 422/82.2; 422/98; 436/55; 436/45

(58) Field of Classification Search ............... 422/807, 422/808, 430, 62, 68.1, 69, 72, 82.01, 82.02, 422/98; 204/400, 412, 228.6, 228.9, 229.1, 204/229.9, 230.1, 230.7, 242; 205/335, 778.5, 205/779.5; 436/55, 45
See application file for complete search history.

(56) References Cited

U.S. PATENT DOCUMENTS

| | | | | |
|---|---|---|---|---|
| 5,002,892 A | * | 3/1991 | Murphy, Jr. .................. | 436/51 |
| 5,006,312 A | * | 4/1991 | Murphy, Jr. .................. | 422/62 |
| 5,075,080 A | * | 12/1991 | Sanders ......................... | 422/70 |

* cited by examiner

*Primary Examiner* — Bruce F Bell
(74) *Attorney, Agent, or Firm* — John A. Fortkort; Fortkort & Houston P.C.

(57) ABSTRACT

A method for measuring an iodine adsorption number of carbon black includes: (a) electrochemically reducing an unknown amount of iodine adsorbed by a predetermined amount of a carbon black sample; (b) measuring the electrical charge used for reducing the unknown amount of the iodine adsorbed by the carbon black sample; and (c) obtaining the iodine adsorption number from the measured electrical charge. An electrolytic cell and a kit for measuring an iodine adsorption number of carbon black are also disclosed.

11 Claims, 2 Drawing Sheets

METHOD FOR MEASURING AN IODINE ADSORPTION NUMBER OF CARBON BLACK, ELECTROLYTIC CELL, AND KIT FOR MEASURING AN IODINE ADSORPTION NUMBER OF CARBON BLACK

BACKGROUND OF THE INVENTION

1. Field of the Invention

This invention relates to a method, an electrolytic cell, and a kit for measuring the iodine adsorption number of carbon black.

2. Description of the Related Art

Carbon black exhibits a large surface area and a high adsorbability by virtue of a plurality of pores formed therein, and thus can be used for the production of various products, for example, an electrode, a catalytic substrate, a pigment, an adsorbent, a rubber intensifier, etc.

The iodine adsorption number is commonly used for evaluating the surface area of carbon black, and the greater the iodine adsorption number, the larger will be the surface area of the carbon black. The industry-accepted standard test for determining the iodine adsorption number of carbon black is set forth in ASTM-D1510. This test is conducted by dispersing a precisely weighted amount of carbon black into an iodine solution that is previously standardized so as to form a mixture, and centrifuging the mixture so as to obtain a supernatant and a precipitate, followed by separating the supernatant from the precipitate. The supernatant thus obtained is subsequently titrated with a standard sodium thiosulfate solution, and the titration volume is recorded in order to calculate the iodine adsorption number. The aforementioned test is disadvantageous in that it requires preparation of the standard sodium thiosulfate solution and that titration of the supernatant is normally conducted manually, which is likely to cause inaccuracy problem in the measured iodine adsorption number attributed to human error. Therefore, there is a need in the art for a method that is efficient and effective in measuring the iodine adsorption number of carbon black and that can eliminate the aforementioned human error.

SUMMARY OF THE INVENTION

Therefore, an object of the present invention is to provide a method, an electrolytic cell, and a kit for measuring an iodine adsorption number of carbon black that can eliminate or alleviate at least one of the above drawbacks associated with the prior art.

According to one aspect of this invention, there is provided a method for measuring an iodine adsorption number of carbon black. The method comprises: (a) electrochemically reducing an unknown amount of iodine adsorbed by a predetermined amount of a carbon black sample; (b) measuring the electrical charge used for reducing the unknown amount of the iodine adsorbed by the carbon black sample; and (c) obtaining the iodine adsorption number from the measured electrical charge.

According to another aspect of this invention, there is provided an electrolytic cell for measuring an iodine adsorption number of carbon black. The electrolytic cell comprises a cathode made from an iodine-adsorbed carbon black sample that contains a predetermined amount of a carbon black sample and iodine adsorbed on the carbon black sample, an anode, and an electrolyte in contact with the cathode and the anode.

According to yet another aspect of this invention, there is provided a kit for measuring an iodine adsorption number of carbon black. The kit comprises an iodine agent to be adsorbed by a carbon black sample, and an electrolytic cell for electrochemically reducing the iodine agent adsorbed by the carbon black sample. The electrolytic cell includes an anode, an electrolyte, and a cathode-connecting conductor adapted for connection with a cathode made from the carbon black sample that adsorbs the iodine agent.

BRIEF DESCRIPTION OF THE DRAWING

Other features and advantages of the present invention will become apparent in the following detailed description of the preferred embodiments of this invention, with reference to the accompanying drawings, in which.

DETAILED DESCRIPTION OF THE PREFERRED EMBODIMENTS

Figure 1:
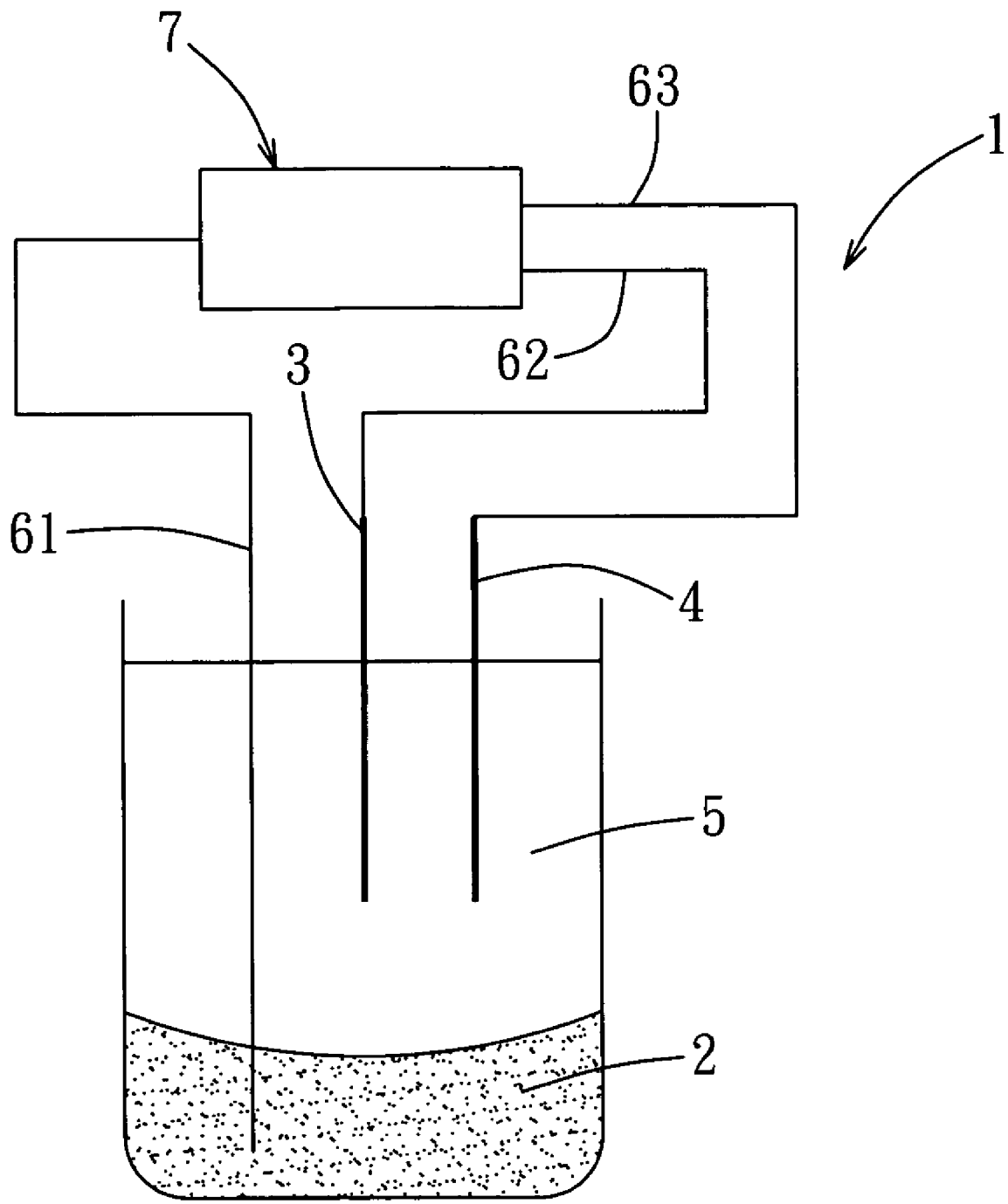
FIG. 1 is a schematic view illustrating the preferred embodiment of an electrolytic cell coupled electrically to a power supply unit of this invention.

A method for measuring an iodine adsorption number of carbon black according to this invention includes: (a) electrochemically reducing an unknown amount of iodine adsorbed by a predetermined amount of a carbon black sample; (b) measuring the electrical charge used for reducing the unknown amount of the iodine adsorbed by the carbon black sample; and (c) obtaining the iodine adsorption number from the measured electrical charge.

Preferably, the method further includes, before step (a), dispersing the carbon black sample into a solution of iodine so that the unknown amount of the iodine is adsorbed by the carbon black sample, and separating the iodine-adsorbed carbon black sample from the solution through centrifuging. Preferably, before the dispersing step, the carbon black sample is subjected to a drying treatment, thereby removing water adsorbed by the carbon black sample. Moreover, to make the carbon black sample completely adsorb iodine, the dispersing step is conducted under stirring, shaking, or ultrasonic vibration. In the solution of iodine, the solvent can be any one capable of dissolving iodine, and preferably, is water.

Preferably, the predetermined amount of the carbon black sample employed in the method ranges from 1 mg to 500 mg; and more preferably, from 10 mg to 30 mg.

Preferably, the centrifuging in the method is conducted at a rotational speed including a centrifugal force ranging from 10 G (gravity force) to 6000 G.

Preferably, the electrochemical reduction in step (a) is conducted in an electrolytic cell that includes an anode, an electrolyte, a cathode-connecting conductor, and a cathode made of the iodine-adsorbed carbon black sample. The cathode-connecting conductor is connected to the cathode, and the electrolyte is in contact with the cathode and the anode.

Preferably, the anode of the electrolytic cell is made from one of metal (such as Pt, Pd, Ru, Ir, etc., or a dimensional stable anode) and a non-metallic conductive material (such as carbon). More preferably, the anode is made from carbon in the form of a rod, a cloth, or a paper so as to prevent iodine produced at the anode from migrating to the cathode.

Preferably, the electrolyte can be solid electrolytes or liquid electrolytes, such as an aqueous solution or an organic solution containing at least one of salts, acids, and bases. When the organic solution is used, the organic solvent thus used can be, e.g., formic acid, acetic acid, acetonitrile, or N,N-dimethylformamide. An aqueous solution of sulfuric acid is commonly used as an electrolyte in the electrochemical field, and preferably, the concentration thereof ranges from $10^{-5}$ M to 10 M. In the preferred embodiments of this invention, the electrolyte is 0.5 M of an aqueous solution of sulfuric acid.

Preferably, the electrolytic cell further includes a reference electrode extending into the electrolyte.

In the electrolytic cell, the electrochemical reduction in step (a) can be conducted by using conventional techniques, for example, by applying a predetermined voltage across the anode and the cathode in a body of the electrolyte of the electrolytic cell, followed by terminating the electrochemical reduction when the current across the cathode approaches 0 A; or by applying a predetermined current across the anode and the cathode, followed by terminating the electrochemical reduction when the potential of the cathode is sharply shifted to a negative value or the potential difference between the anode and the cathode is sharply increased. When a reference electrode is used, a voltage is applied for controlling the potential of the cathode corresponding to the reference electrode. The potential of the cathode is set to be more negative than reduction potential of iodine, and be more positive than the decomposition potential of the electrolyte at the cathode. For example, when the electrolyte is an aqueous solution, the reference electrode is a saturated calomel electrode (SCE), the potential of the cathode is more negative than SCE by 0.4V, and is more positive than the potential for generating a hydrogen gas (which varies with the pH value of the aqueous solution) at the cathode.

In one preferred embodiment of this invention, the electrochemical reduction in step (a) is conducted by applying a predetermined voltage across the anode and the cathode, and the total electrical charge for reducing the unknown amount of the iodine adsorbed by the carbon black sample is measured by monitoring the variations of the current with respect to the reduction time, followed by calculating the iodine adsorption number per gram of the carbon black sample in accordance with the formula (A) $I=(Q_S/W_S-Q_B/W_B) \times E$, in which I represents the iodine adsorption number per gram of the carbon black sample; $Q_S$ represents an area in a current-time plot (as illustrated by the shaded area (S1) in FIG. 2, i.e., the total electrical charge for reducing the iodine) for the iodine-adsorbed carbon black sample; $W_S$ represents the weight of the predetermined amount of the carbon black sample in a unit of gram; $Q_B$ represents an area in a current-time plot (as illustrated by the shaded area (S2) in FIG. 2, i.e., the total electrical charge for reducing the iodine) for a blank of carbon black, i.e., without iodine; $W_B$ represents the weight of the predetermined amount of the blank of carbon black in a unit of gram; and E represents the electrochemical equivalent of iodine and is 1.315 mg/coulomb.

FIG. 1 illustrates one preferred embodiment of the electrolytic cell 1 coupled electrically to a power supply unit 7. The electrolytic cell 1 includes a cathode 2 made from the carbon black sample with iodine adsorbed therein, an anode 3, a reference electrode 4, an electrolyte 5, a cathode-connecting conductor 61, an anode-connecting conductor 62, and a reference electrode-connecting conductor 63. The power supply unit 7 is coupled electrically to the conductors 61~63.

A kit that can be used to carry out the method of measuring iodine absorption number of carbon black according to the present invention includes an iodine agent to be adsorbed by a carbon black sample, and an electrolytic cell for electrochemically reducing the iodine agent to be adsorbed by the carbon black sample. The electrolytic cell includes an anode, an electrolyte, and a cathode-connecting conductor adapted for connection with the carbon black sample which adsorbs the iodine agent.

The following examples are provided to illustrate the merits of the preferred embodiments of the invention, and should not be construed as limiting the scope of the invention.

EXAMPLES

Example 1-1 (E1-1)

Real Test for Obtaining $Q_S$ of Formula (A)

An iodine solution having a concentration of 0.0473 N was prepared by mixing 6 g of $I_2$ (purchased from Sigma-Aldrich), 57 g of KI (purchased from Sigma-Aldrich), and 1000 mL of distilled water. 10.09 mg of a carbon black sample (model name: XC-72, purchased from Cabot Corp., U.S.A.) was dried at 125° C. for one hour, and added into 1.0 mL of the iodine solution in a test tube. The mixture was subjected to ultrasonic vibration for about 5 min so as to allow iodine to be adsorbed by the carbon black sample. The mixture in the test tube was centrifuged at a rotational speed inducing a centrifugal force of 250 G for 3 min, followed by removal of the supernatant. The precipitate of the iodine-adsorbed carbon black in the test tube was cleaned with deionized water for serving as a cathode in the subsequent iodine reducing process.

8.0 mL of an aqueous solution of sulfuric acid having a concentration of 0.5 M was added into the test tube for serving as an electrolyte in the subsequent iodine reducing process. An active carbon fiber electrode (model No.: 1002-CC-S, purchased from Beam Associate Co.) and a saturated calomel electrode (model No.: HS-205C, purchased from TOA ELECTRONICS, LTD., JAPAN) were disposed in the sulfuric acid solution in the test tube to serve as an anode and a reference electrode, respectively, in the subsequent iodine reducing process. The cathode, anode, and reference electrodes were electrically coupled to a power supply unit (model No.: Autolab-PGSTAT30, purchased from Eco Chemie Co.) with platinum wires, to conduct the iodine reducing process.

Figure 2:
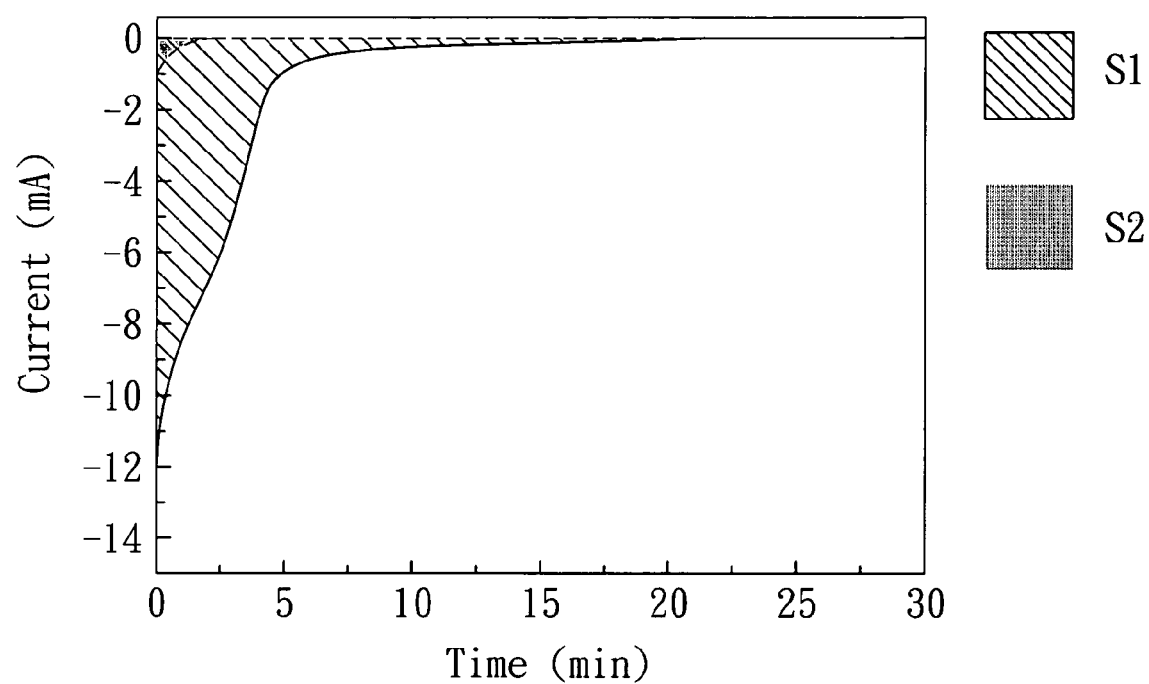
FIG. 2 is an analysis plot of a reducing current vs. time to illustrate the test results of Example 1.

In the reducing process, a voltage was applied across the anode and the cathode so as to ensure that the potential of the cathode is 0.0 V with respect to SCE, and was terminated when the current across the cathode approached 0 A. The variation of the current across the anode and the cathode along with time during the reduction was recorded and was plotted against time to obtain a curve (the solid line) shown in FIG. 2. The shaded area (S1) in FIG. 2 represents $Q_S$ and is 2.01 coulomb.

Blank Test for Obtaining $Q_B$ of Formula (A)

The procedure and conditions for obtaining $Q_B$ of Formula (A) were similar to those for $Q_S$ of Formula (A) except that the amount of carbon black employed was 10.64 mg, and that aqueous sulfuric acid solution (0.5M) was used to replace the iodine solution. The variation of the current across the anode and the cathode along with time during the reduction was recorded and was plotted against time to obtain a curve (the dashed line) shown in FIG. 2. The shaded area (S2) in FIG. 2 represents $Q_B$ and is 0.16 coulomb.

Calculation of the Iodine Adsorption Number

The iodine adsorption number per gram of the carbon black sample (denoted by "I") was calculated according to Formula (A). The result is shown in Table 1.

Examples 1-2~1-6 (E1-2~E1-6)

The procedures and the conditions in measuring the iodine adsorption number of E1-2~E1-6 were similar to those of E1-1, except that, in E1-2~E1-6, the amount of the carbon black sample employed in each of E1-2~E1-6 was changed as listed in Table 1. The calculated results of the values of I for E1-2~E1-6 are shown in Table 1.

TABLE 1

| Example No. | Amount of carbon black sample (mg) | Electrical charge (coulomb) | Iodine adsorption number (mg of $I_2$/g of C) |
|---|---|---|---|
| E1-1 | 10.09 | 2.01 | 242 |
| E1-2 | 10.28 | 2.04 | 241 |
| E1-3 | 10.05 | 1.97 | 238 |
| E1-4 | 10.01 | 2.00 | 243 |
| E1-5 | 9.61 | 1.95 | 247 |
| E1-6 | 9.85 | 1.97 | 243 |
| Average | | | 242.3 |

As shown in Table 1, the average iodine adsorption number per gram of the carbon black sample of the set of E1-1~E1-6 is 242.3 mg as compared to 240 mg per gram of the carbon black sample determined by the titration method according to the standard of ASTM-D1510.

Examples 2-1~2-5, 3-1~3-5, 4-1~4-5 (E2-1~E2-5, E3-1~E3-5, E4-1~E4-5)

The procedures and the conditions in measuring the iodine adsorption number for the set of E2-1~E2-5, the set of E3-1~E3-5, and the set of E4-1~E4-5 were similar to those of E1-1, except that in these Examples, the sources and the amounts of the carbon black samples employed in these Examples were changed as listed in Tables 2~4, respectively. In addition, the amounts of carbon black employed in the blank tests for the set of E2-1~E2-5, the set of E3-1~E3-5, and the set of E4-1~E4-5 were 10.21 mg, 9.91 mg, and 10.06 mg, respectively. The values of $Q_B$ thus obtained for the set of E2-1~E2-5, the set of E3-1~E3-5, and the set of E4-1~E4-5 are 0.05 coulomb, 0.11 coulomb, and 0.04 coulomb, respectively.

The calculated results of the values of I for the set of E2-1~E2-5, the set of E3-1~E3-5, and the set of E4-1~E4-5 are shown in Tables 2~4, respectively.

TABLE 2

| Model name of carbon black | Example No. | Amount of carbon black sample (mg) | Electrical charge (coulomb) | Iodine adsorption number (mg of $I_2$/g of C) |
|---|---|---|---|---|
| R-660[a] | E2-1 | 10.07 | 1.01 | 125 |
| | E2-2 | 10.40 | 1.01 | 121 |
| | E2-3 | 9.69 | 0.96 | 124 |
| | E2-4 | 9.70 | 0.99 | 128 |
| | E2-5 | 9.57 | 0.96 | 126 |
| Average | | | | 124.8 |

[a]R-660 was purchased from Cabot Corp., U.S.A.

As shown in Table 2, the average iodine adsorption number per gram of the carbon black of the set of E2-1~E2-5 is 124.8 mg as compared to 126 mg per gram of the carbon black sample determined by the titration method according to the standard of ASTM-D1510.

TABLE 3

| Model name of carbon black | Example No. | Amount of carbon black sample (mg) | Electrical charge (coulomb) | Iodine adsorption number (mg of $I_2$/g of C) |
|---|---|---|---|---|
| N-110[b] | E3-1 | 10.29 | 1.29 | 151 |
| | E3-2 | 10.20 | 1.29 | 151 |
| | E3-3 | 10.03 | 1.3 | 156 |
| | E3-4 | 9.82 | 1.20 | 147 |
| | E3-5 | 9.98 | 1.24 | 149 |
| Average | | | | 150.8 |

[b]N-110 was purchased from China Synthetic Rubber Corp., R.O.C.

As shown in Table 3, the average iodine adsorption number per gram of the carbon black of the set of E3-1~E3-5 is 150.8 mg as compared to 153 mg per gram of the carbon black sample determined by the titration method according to the standard of ASTM-D1510.

TABLE 4

| Model name of carbon black | Example No. | Amount of carbon black sample (mg) | Electrical charge (coulomb) | Iodine adsorption number (mg of $I_2$/g of C) |
|---|---|---|---|---|
| N-774[c] | E4-1 | 10.42 | 0.36 | 40 |
| | E4-2 | 10.39 | 0.35 | 39 |
| | E4-3 | 9.98 | 0.36 | 42 |
| | E4-4 | 9.80 | 0.34 | 41 |
| | E4-5 | 9.78 | 0.36 | 43 |
| Average | | | | 41 |

[c]N-774 was purchased from China Synthetic Rubber Corp., R.O.C.

As shown in Table 4, the average iodine adsorption number per gram of the carbon black sample of the set of E4-1~E4-5 is 41 mg as compared to 40 mg per gram of the carbon black sample determined by the titration method according to the standard of ASTM-D1510.

In conclusion, the method of this invention involving electrochemically reducing iodine adsorbed in the carbon black sample to measure the iodine adsorption number of carbon black can eliminate or alleviate the aforementioned drawbacks, such as preparation of the standard sodium thiosulfate solution for titration and the human error during titration, associated with the conventional titration method. Moreover, comparison of the results of the iodine adsorption number obtained from the method of this invention with those obtained from the titration method of ASTM-D1510 further proves that the method of this invention is workable and reliable.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for measuring an iodine adsorption number of carbon black, comprising:
   (a) electrochemically reducing an unknown amount of iodine adsorbed by a predetermined amount of a carbon black sample;
   (b) measuring the electrical charge used for reducing the unknown amount of the iodine adsorbed by the carbon black sample; and
   (c) obtaining the iodine adsorption number from the measured electrical charge.

2. The method of claim 1, further comprising, before step (a), dispersing the carbon black sample into a solution of iodine so that the unknown amount of the iodine is adsorbed by the carbon black sample, and separating the iodine-adsorbed carbon black sample from the solution through centrifuging.

3. The method of claim 2, wherein the electrochemical reduction in step (a) is conducted in an electrolytic cell including a cathode defined by the iodine-adsorbed carbon black sample.

4. The method of claim 3, wherein the electrochemical reduction in step (a) is conducted by applying a predetermined voltage across an anode and the cathode in a body of an electrolyte of the electrolytic cell, and is terminated when the current across the cathode approaches 0 A.

5. The method of claim 4, wherein the anode of the electrolytic cell is made from one of metal and a non-metallic conductive material.

6. The method of claim 3, wherein the electrolytic cell further includes a reference electrode, and the electrochemical reduction in step (a) is conducted by setting the cathode potential at a predetermined value with respect to said reference electrode, and is terminated when the current across the cathode approaches 0 A.

7. The method of claim 2, wherein the centrifuging is conducted at a rotational speed inducing a centrifugal force ranging from 10 G to 6000 G.

8. An electrolytic cell for measuring an iodine adsorption number of carbon black, comprising:
   a cathode made from an iodine-adsorbed carbon black sample that contains a predetermined amount of a carbon black sample and iodine adsorbed on said carbon black sample;
   an anode; and
   an electrolyte in contact with said cathode and said anode.

9. The electrolytic cell of claim 8, further comprising a reference electrode extending into said electrolyte.

10. A kit for measuring an iodine adsorption number of carbon black, comprising:
    an iodine agent to be adsorbed by a carbon black sample and
    an electrolytic cell for electrochemically reducing the iodine agent adsorbed by the carbon black sample, the electrolytic cell including an anode, an electrolyte, and a cathode-connecting conductor adapted for connection with a cathode made from the carbon black sample that adsorbs the iodine agent.

11. The kit of claim 10, wherein said electrolytic cell further includes a reference electrode extending into said electrolyte.

* * * * *